US008956278B2

(12) United States Patent
Torrie et al.

(10) Patent No.: US 8,956,278 B2
(45) Date of Patent: Feb. 17, 2015

(54) MULTIPLE PORTAL GUIDE

(75) Inventors: Paul Alexander Torrie, Marblehead, MA (US); Richard Villar, London (GB); Victor Ilizaliturri, Mexico City (MX)

(73) Assignee: Smith & Nephew, Inc., Memphis, TN (US)

( * ) Notice: Subject to any disclaimer, the term of this patent is extended or adjusted under 35 U.S.C. 154(b) by 1200 days.

(21) Appl. No.: 12/032,168

(22) Filed: Feb. 15, 2008

(65) Prior Publication Data
US 2009/0163766 A1 Jun. 25, 2009

Related U.S. Application Data

(60) Provisional application No. 61/015,811, filed on Dec. 21, 2007.

(51) Int. Cl.
*A61B 1/00* (2006.01)
*A61B 17/17* (2006.01)
*A61B 1/04* (2006.01)
*A61B 19/00* (2006.01)

(52) U.S. Cl.
CPC ........... *A61B 17/175* (2013.01); *A61B 17/1714* (2013.01); *A61B 17/1739* (2013.01); *A61B 19/201* (2013.01)
USPC .......................................... 600/102; 600/114

(58) Field of Classification Search
USPC .................................. 600/102, 114
See application file for complete search history.

(56) References Cited

U.S. PATENT DOCUMENTS

| 3,299,883 | A | * | 1/1967 | Rubens .......................... 600/102 |
| 4,254,762 | A | * | 3/1981 | Yoon .............................. 600/114 |
| 4,899,756 | A | | 2/1990 | Sonek |
| 5,562,664 | A | | 10/1996 | Durlacher et al. |
| 5,665,072 | A | * | 9/1997 | Yoon ......................... 604/164.12 |
| 5,681,320 | A | | 10/1997 | McGuire |
| 5,688,284 | A | | 11/1997 | Chervitz et al. |
| 5,829,444 | A | | 11/1998 | Ferre et al. |
| 5,968,050 | A | | 10/1999 | Torrie |
| 6,120,511 | A | | 9/2000 | Chan |

(Continued)

FOREIGN PATENT DOCUMENTS

| EP | 1649818 A2 | 4/2006 |
| EP | 1882456 A2 | 1/2008 |

(Continued)

OTHER PUBLICATIONS

International Search Report and Written Opinion for International Patent Application PCT/US2011/038351 mailed Oct. 24, 2011.

(Continued)

*Primary Examiner* — Alireza Nia
(74) *Attorney, Agent, or Firm* — Burns & Levinson LLP; Joseph M. Maraia; Weber Hsiao

(57) ABSTRACT

The present disclosure relates to a guide assembly including a guide having a body and a joint including at least one through hole, wherein the joint is configured for sliding along a length of the body, and a first surgical device. The guide is coupled to the first surgical device and a longitudinal axis of the through hole is co-radial with an end of the first surgical device. Other guide assemblies and methods of creating multiple portals during surgery are also disclosed.

30 Claims, 16 Drawing Sheets

(56) References Cited

U.S. PATENT DOCUMENTS

| | | | |
|---|---|---|---|
| 6,132,368 A * | 10/2000 | Cooper | 600/102 |
| 6,187,011 B1 | 2/2001 | Torrie | |
| 6,216,029 B1 | 4/2001 | Paltieli | |
| 6,490,467 B1 | 12/2002 | Bucholz et al. | |
| 6,958,067 B2 | 10/2005 | Whittaker et al. | |
| 7,201,756 B2 * | 4/2007 | Ross et al. | 606/96 |
| 2002/0143341 A1 | 10/2002 | Biedermann et al. | |
| 2002/0143342 A1 | 10/2002 | Hangody et al. | |
| 2002/0156376 A1 | 10/2002 | Wang et al. | |
| 2002/0173849 A1 | 11/2002 | McKernan et al. | |
| 2003/0208206 A1 * | 11/2003 | Gitis et al. | 606/108 |
| 2004/0193172 A1 | 9/2004 | Ross et al. | |
| 2004/0220588 A1 | 11/2004 | Kermode | |
| 2006/0195112 A1 | 8/2006 | Ek | |
| 2008/0027457 A1 | 1/2008 | Dienst et al. | |
| 2009/0163766 A1 | 6/2009 | Torrie | |
| 2010/0241106 A1 | 9/2010 | Torrie | |

FOREIGN PATENT DOCUMENTS

| | | |
|---|---|---|
| FR | 2716364 A1 | 8/1995 |
| FR | 2901465 A1 | 11/2007 |
| WO | WO0182838 A2 | 11/2001 |
| WO | WO2006074321 A3 | 1/2007 |
| WO | WO2011153094 A1 | 12/2011 |

OTHER PUBLICATIONS

Office Action for U.S. Appl. No. 12/794,142, mailed Jan. 16, 2013.
Victor M. Ilizaliturri, Jr., M.D., et al, "An Aiming Guide for Anterior Portal Placement in Hip Arthroscopy", Arthroscopy: The Journal of Arthroscopic and Related Surgery, vol. 19, No. 9 Nov. 2003: E77.
Michael Dienst, M.D., et al, "Safe Arthroscopic Access to the Central Compartment of the Hip", Arthroscopy: The Journal of Arthoscopic and Related Surgery, vol. 21, No. 12 Dec. 2005: pp. 1510-1514.
J.W. Thomas Byrd, M.D., et al, Hip Arthroscopy: An Anatomic Study of Portal Placement and Relationship to the Extra-Articular Structures, Arthroscopy: The Journal of Arthroscopic and Related Surgery, vol. 11, No. 4 Aug. 1995: pp. 418-423.
Victor M. Illizaliturri, Jr., M.D., "Hip Arthroscopy Using the Smith & Nephew Hip Access System", Smith & Nephew Hip Series Technique Guide© 2004.
J.W. Thomas Byrd, M.D., "Hip Arthroscopy Principles and Application", Smith & Nephew Hip Series Technique Guide© 2001.
International Search Report and Written Opinion for International Application No. PCT/US2011/038351, mailed Oct. 24, 2011.
Office Action for U.S. Appl. No. 12/794,142, mailed Aug. 3, 2012.
International Search Report and Written Opinion for International Application No. PCT/US2012/028537, mailed May 25, 2012.
International Preliminary Report on Patentability for International Application No. PCT/US2011/038351, mailed Dec. 4, 2012.
Notice of Reasons for Rejection for Japanese Application No. 2010-539524, mailed Oct. 9, 2012.
Thomas G. Sampson, M.D., "Arthroscopic Treatment of Femoracetabular Impingement," Smith & Nephew Hip Series Technique Guide© 2006.
Patent Examination Report No. 1 for Australian Patent Application No. 2008341062, mailed Mar. 20, 2013.
Notice of Reasons for Rejections for Japanese Patent Application No. 2010-539524, mailed Mar. 20, 2013.
Second Office Action for Japanese Patent Application No. 2010-539524, mailing date Apr. 16, 2013.
Third Office Action for Japanese Patent Application No. 2010-539524, mailing date Nov. 26, 2013.
Decision of Rejection for Japanese Patent Application No. 2010-539524, mailing date Jun. 2, 2014.
First Office Action for Chinese application 201180038188.3, mailing date Sep. 28, 2014.

* cited by examiner

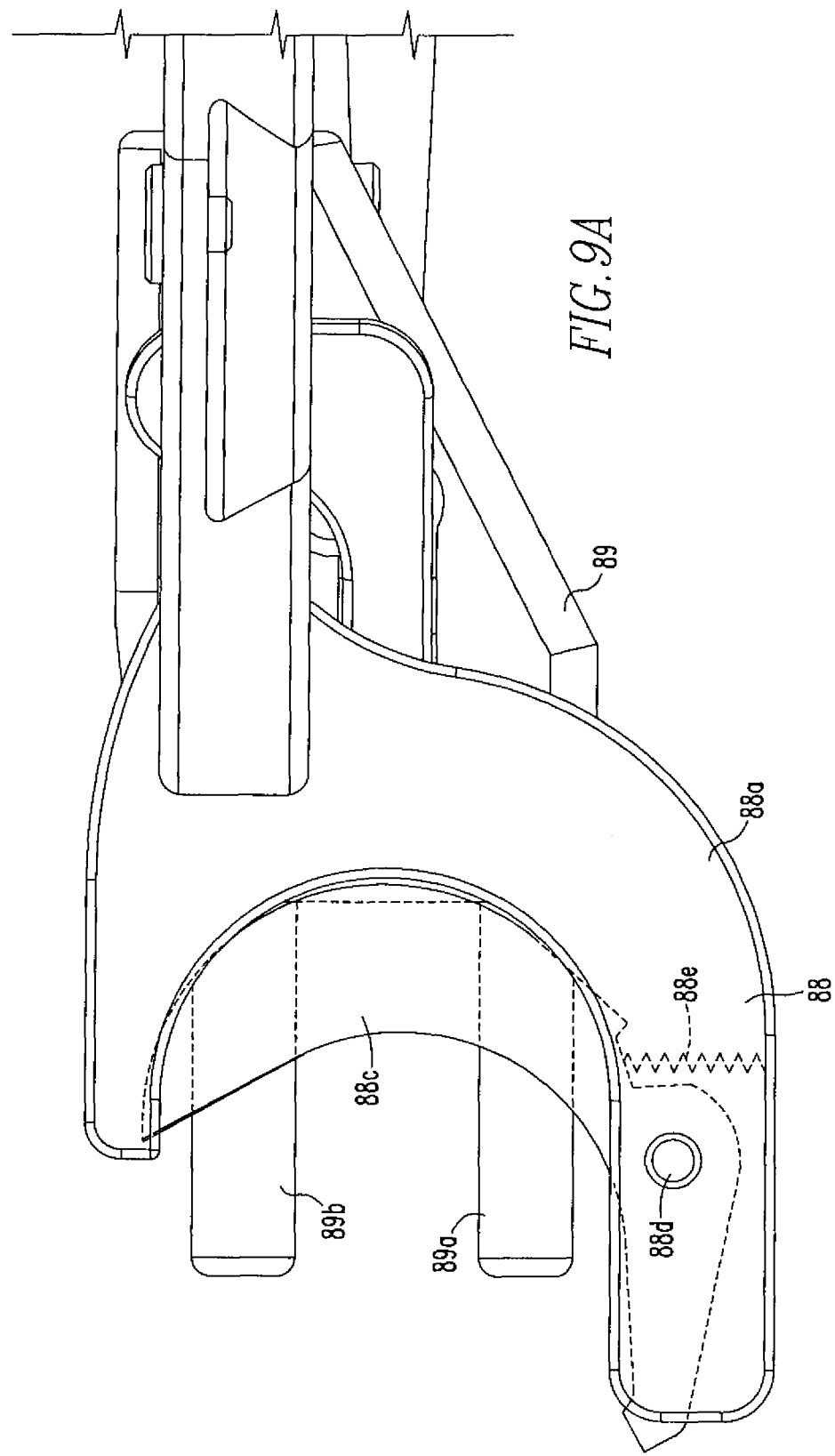

MULTIPLE PORTAL GUIDE

CROSS-REFERENCE TO RELATED APPLICATIONS

This application claims the benefit of U.S. Provisional Application No. 61/015,811, filed Dec. 21, 2007, the disclosure of which is incorporated by reference herein in its entirety.

BACKGROUND OF THE INVENTION

1. Field of the Invention

The present disclosure relates to medical devices for use in surgery and, more specifically, a guide for use in creating multiple portals during surgery.

2. Related Art

During arthroscopic surgery, the joint areas of the body, such as the hip, knee, shoulder, and other joint areas, are approached via the use of an endoscope. Some joints are harder to access than others. For example, the hip joint differs from other joints in that a much thicker layer of soft tissue, known as the hip capsule, surrounds it. This thick layer makes changing the trajectory of instruments placed into the joint difficult and the importance of placing portals, or tissue passages, more critical than other joints.

Presently, fluoroscopy is used to place the portals that house the endoscope and the other instruments used during surgery. Multiple x-rays are taken while the surgeon tries various approaches to the joint using a thin needle that may be reinserted several times until the ideal portal placement is found. This process exposes the surgical team to radiation, is time consuming, and can lead to trauma, particularly to the delicate articular cartilage and, in the case of the hip joint, the acetabular labrum.

There is a need for an apparatus and method that would allow for the creation of multiple portals while substantially reducing the possible harmful effects and the amount of time that is required of the present methods.

SUMMARY OF THE INVENTION

In one aspect, the present disclosure relates to a guide assembly including a guide having a body and a joint including at least one through hole, wherein the joint is configured for sliding along a length of the body, and a first surgical device. The guide is coupled to the first surgical device and a longitudinal axis of the through hole is co-radial with an end of the first surgical device.

In an embodiment, the guide assembly further includes a mechanism for locking the joint in a position along the body. In another embodiment, the guide assembly further includes a second surgical device, such as a second cannula, disposed within the through hole, wherein the second surgical device includes a longitudinal axis that is co-radial with the end of the first surgical device. In yet another embodiment, the first surgical device is disposed within a first cannula such that the end of the first surgical device protrudes through an end of the first cannula. In yet a further embodiment, the longitudinal axis of the through hole is co-radial with a point that is offset a distance, about 1 cm, from the end of the first surgical device. The first surgical device may include an endoscope, wherein the point is offset a distance, about 1 cm, in a direction of view of the endoscope. In an embodiment, the guide is coupled to the first cannula. In another embodiment, the end of the first cannula includes a pointed tip offset a distance, about 1 cm, from the end of the first surgical device. In yet another embodiment, the first surgical device includes an endoscope, wherein the pointed tip is offset a distance, about 1 cm, in a direction of view from the endoscope.

In another embodiment, the second surgical device includes a second cannula. In an embodiment, the second cannula includes a needle, wherein the needle includes a first end and a second end and is slidably disposed within the second cannula. In another embodiment, the needle includes a first end, which may have a depth stop, and a second end that intersects an end of the first surgical device. In an embodiment, the second end of the needle does not advance past the end of the first surgical device. In a further embodiment, the body includes a first attachment portion located at a first end of the body and a second attachment portion located near a second end of the body, wherein the first attachment portion and the second attachment portion are configured for coupling the body to the first surgical device. In yet a further embodiment, the second end of the body does not extend beyond a plane located between the second attachment portion and a longitudinal axis of the first surgical device. In yet a further embodiment, an angle β, which may be about 60°, exists between the longitudinal axis of the first surgical device and the plane.

In yet an even further embodiment, the first attachment portion includes a lever arm configured for coupling of the first surgical device to the first attachment portion. The lever arm is movable between a first position and a second position with respect to the first attachment portion, wherein the first surgical device is coupled to the first attachment portion when the lever arm is in a second position.

In yet a further embodiment, a longitudinal axis of the through hole is co-radial with a point that is offset a distance, about 1 cm, from the end of the first surgical device. In an embodiment, the first surgical device includes an endoscope, wherein the point offset a distance, about 1 cm, in a direction of view of the endoscope.

In another aspect, the present disclosure relates to a guide assembly including a guide having a body with at least one through hole and a first surgical device, wherein the guide is coupled to the first surgical device and a longitudinal axis of the through hole is co-radial with an end of the first surgical device. In an embodiment, the body includes multiple through holes and each through hole includes a longitudinal axis that is co-radial with the end of the first surgical device. In another embodiment, the first surgical device is disposed within a first cannula such that the end of the first surgical device protrudes through an end of the first cannula. In yet another embodiment, the end of the first cannula includes a pointed tip offset a distance, about 1 cm, from the end of the first surgical device. In a further embodiment, the first surgical device includes an endoscope, wherein the pointed tip is offset a distance, about 1 cm, in a direction of view of the endoscope. In yet a further embodiment, the first surgical device includes an aimer arm. In an embodiment, the aimer arm rotates about a longitudinal axis of the aimer arm. In another embodiment, a second surgical device is disposed within the through hole, wherein the second surgical device includes a longitudinal axis that is co-radial with a distal end of the aimer. In yet another embodiment, the second surgical device includes a second cannula, wherein the second cannula includes a depth stop coupled to the second cannula. In a further embodiment, a needle is disposed within the second cannula and an end of the needle does not advance past the end of the first surgical device.

In yet another aspect, the present disclosure relates to a method of creating multiple portals during surgery. The method includes creating a first portal in tissue; inserting a first surgical device through the first portal; coupling a guide to a first end of the first surgical device, the guide including a body having at least one through hole, wherein a longitudinal axis of the through hole is co-radial with an end of the first surgical device; and inserting a second surgical device through the hole and into the tissue to create a second portal.

In an embodiment, the second surgical device is co-radial with the end of the first surgical device. In another embodiment, the body includes multiple through holes. In yet another embodiment, each through hole includes a longitudinal axis that is co-radial with the end of the first surgical device. In a further embodiment, the first surgical device is disposed within a first cannula such that the end of the first surgical device protrudes through an end of the first cannula. In yet a further embodiment, the end of the first cannula includes a pointed tip, wherein the pointed tip is offset a distance, about 1 cm, in a direction of view of the endoscope. In an embodiment, the first surgical device includes an endoscope, wherein the pointed tip is offset a distance in a direction of view of the endoscope. In another embodiment, a longitudinal axis of the through hole is co-radial with the pointed tip. In yet another embodiment, the first surgical device includes an endoscope, wherein a longitudinal axis of the through hole is co-radial with a point that is offset a distance, about 1 cm, from the end of the endoscope.

In yet another embodiment, the second surgical device includes a second cannula. In a further embodiment, the second cannula includes a depth stop coupled to the second cannula. In yet a further embodiment, the first surgical device includes an aimer arm, the aimer arm having a distal end. In an embodiment, the aimer arm rotates about a longitudinal axis of the aimer arm. In another embodiment, the second surgical device includes a longitudinal axis that is co-radial with a distal end of the aimer arm. In yet another embodiment, a needle is disposed within the second cannula and an end of the needle does not advance past the end of the first surgical device.

In yet another aspect, the present disclosure relates to a method of creating multiple portals during surgery. The method includes creating a first portal in tissue; inserting a first surgical device through the first portal; coupling a guide to a first end of the first surgical device, the guide including a body and a joint including at least one through hole wherein a longitudinal axis of the through hole is co-radial with an end of the first surgical device; and inserting a second surgical device through the hole and into the tissue to create a second portal.

In an embodiment, the guide includes a mechanism for locking the joint in a position along the body, the method further including sliding the joint along the body to the position and locking the joint in the position before creating the second portal.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings.

FIG. 9A shows a top view of the lever arm, of the fourth guide assembly, in a first position.

DETAILED DESCRIPTION OF THE EMBODIMENTS

The following description of the preferred embodiment(s) is merely exemplary in nature and is in no way intended to limit the disclosure, its application, or uses.

Figure 1:
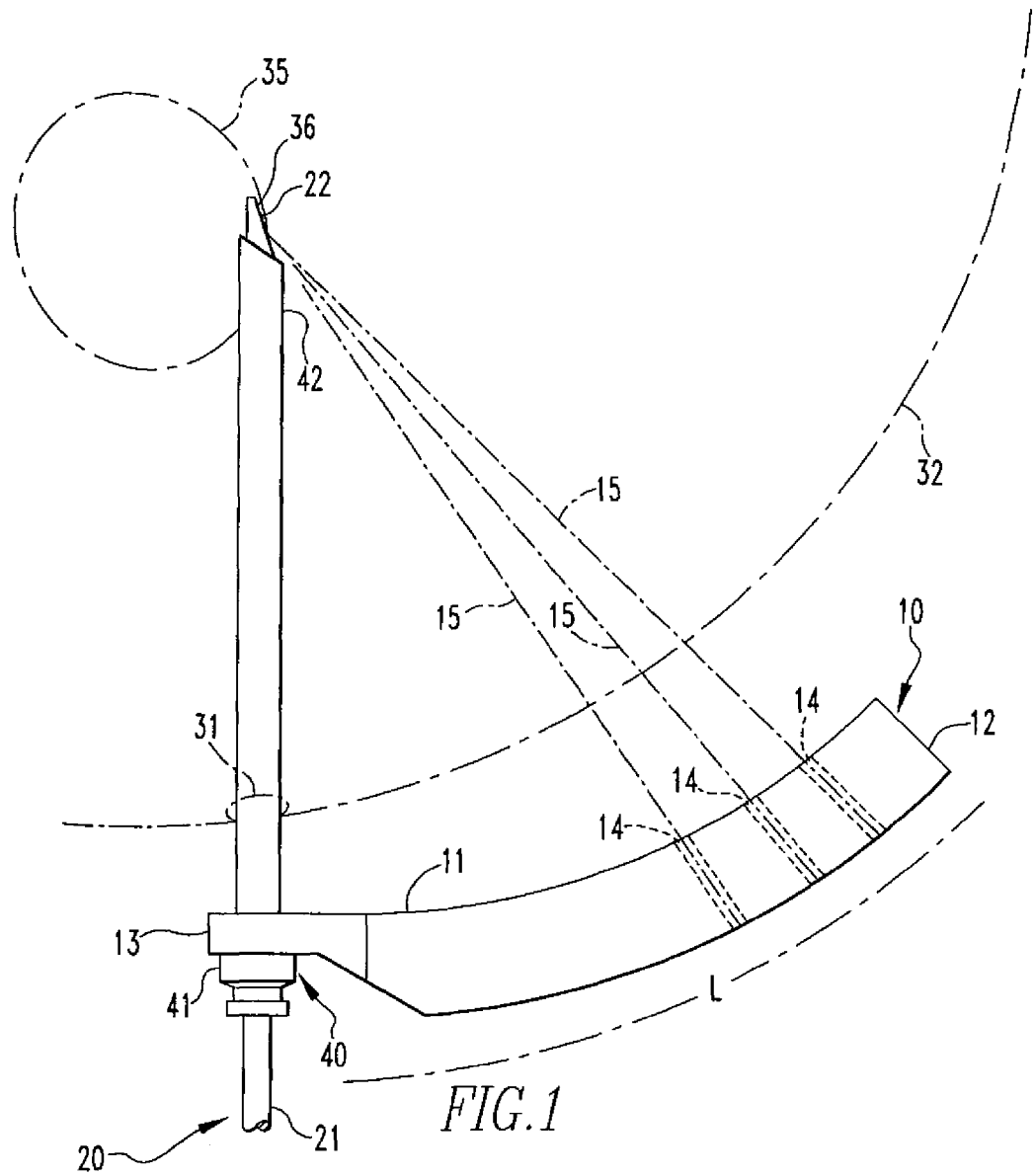
FIGS. 1-4 show front views of a first guide assembly of the present disclosure.

FIG. 1 shows a guide 10 that includes a body 11 having a first end 12, a second end 13, an arc along a length L of the body 11, and at least one through hole 14. Also shown in FIG. 1 is a first surgical instrument 20, such as an endoscope, that includes a first end 21 and a second end 22. The second end 13 of the guide 10 is coupled to the first end 21 of the endoscope 20, via a cannula 40, as further described below, and a longitudinal axis 15 of the through hole 14 intersects, or is co-radial with, the second end 22 of the endoscope 20. As also shown in FIG. 1, the body 11 may include multiple through holes 14, each of which includes a longitudinal axis 15 that intersects, or is co-radial with, the second end 22 of the endoscope 20.

During arthroscopic surgery, especially hip arthroscopy, a first portal 31 is created in a relatively safe position, within a patient's body 32, where damage to internal structures is minimized. The portal 31 may be created via the use of fluoroscopy, as described above, or another method known to one of ordinary skill in the art. The first cannula 40 and endoscope 20 are then inserted through the portal 31, so that a clear view of the inside of the patient's body 32, especially the area 35 where surgery is to be performed (i.e. the hip joint and the capsule surrounding the joint), can be seen by the surgeon. This view also shows the surgeon the anatomy that must be avoided and where a safe area for placing other portals is. As will be further discussed below, the endoscope 20 is disposed within the first cannula 40 such that the second end 22 of the endoscope 20 protrudes through a second end 42 of the cannula 40. After positioning the second end 22 of the endoscope 20 at an area 36 where the surgeon wishes a second portal (FIG. 4, 33) to be placed, such as the inner surface of the hip capsule, the guide 10 is coupled to the first end 21 of the endoscope 20, via the cannula, and the second portal (FIG. 4, 33) is placed relative to the second end 22 of the endoscope 20 by inserting a second surgical device (FIG. 4, 34), such as a second cannula, through one of the through holes 14 and into the patient's body 32. Since the longitudinal axis 15 of the through hole 14 intersects, or is co-radial with, the second end 22 of the endoscope 20, the second cannula 34 would also be co-radial with the second end 22 of the endoscope 20. Furthermore, and as will be described below, this co-radial relationship between the second cannula 34 and the second end 22 of the endoscope 20 allows a needle or other surgical instrument that may be placed within the second cannula 34 and used in the area 35 described above, to intersect the second end 22 of the endoscope 20.

Having multiple through holes 14 in the guide 10 allows for flexibility in the placement of the second portal 33 so that damage to internal structures can be minimized. However, a guide 10 having only one through hole 14 may be used.

Figure 2:
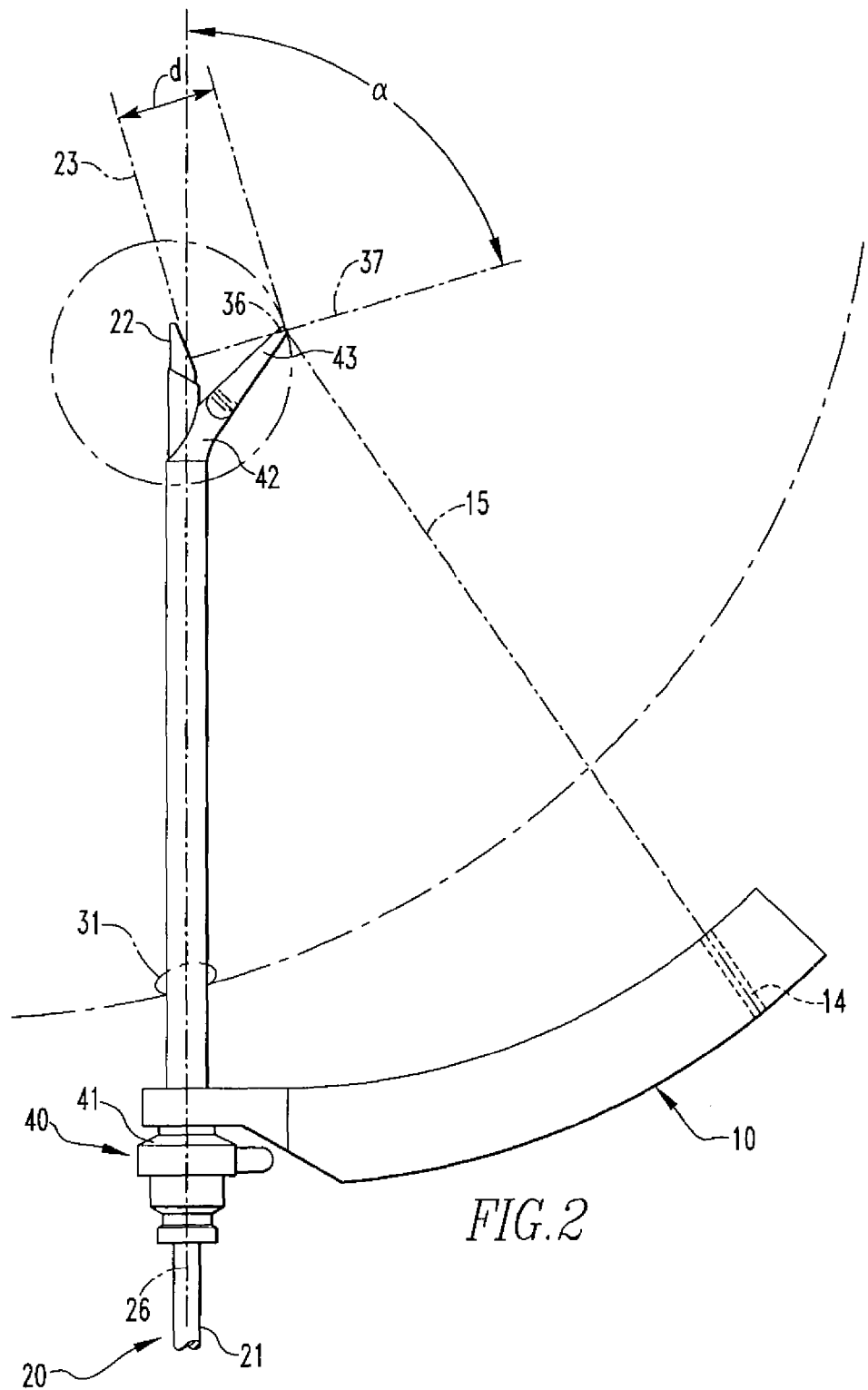

FIG. 2 shows the endoscope 20 disposed within the first cannula 40, as described above, such that the second end 22 of the endoscope 20 protrudes through a second end 42 of the cannula 40. The guide 10 is coupled to a first end 41 of the first cannula 40. The cannula 40 has a pointed tip 43, located at the second end 42, which is offset a distance d from the endoscope 20 or in a direction of view 37 of the endoscope 20. As shown in FIG. 2 and in subsequent figures, as described below, the distance d is measured from the optical center 23 of the endoscope 20. The direction of view 37 of the endoscope 20 is located at an angle α, about 70°, relative to a longitudinal axis 26 of the endoscope 20. Sometimes, the anatomy of the body prevents the second end 22 of the endoscope 20 from being positioned in the area 36, such as the inner surface of the hip capsule as described above, where the surgeon wishes the second portal (FIG. 4, 33) to be placed. When this happens, the cannula 40 with the pointed tip 43 can be used to identify this area 36 and a longitudinal axis 15 of the guide through hole 14 could be made to intersect, or be co-radial with, the pointed tip 43. Rather than using a cannula with a pointed tip, the endoscope 20 could be fitted with a pointed tip similar to the pointed tip 43 of the cannula 40. The endoscope 20 and pointed tip could be introduced into the patient's body via a slotted cannula.

Figure 3:
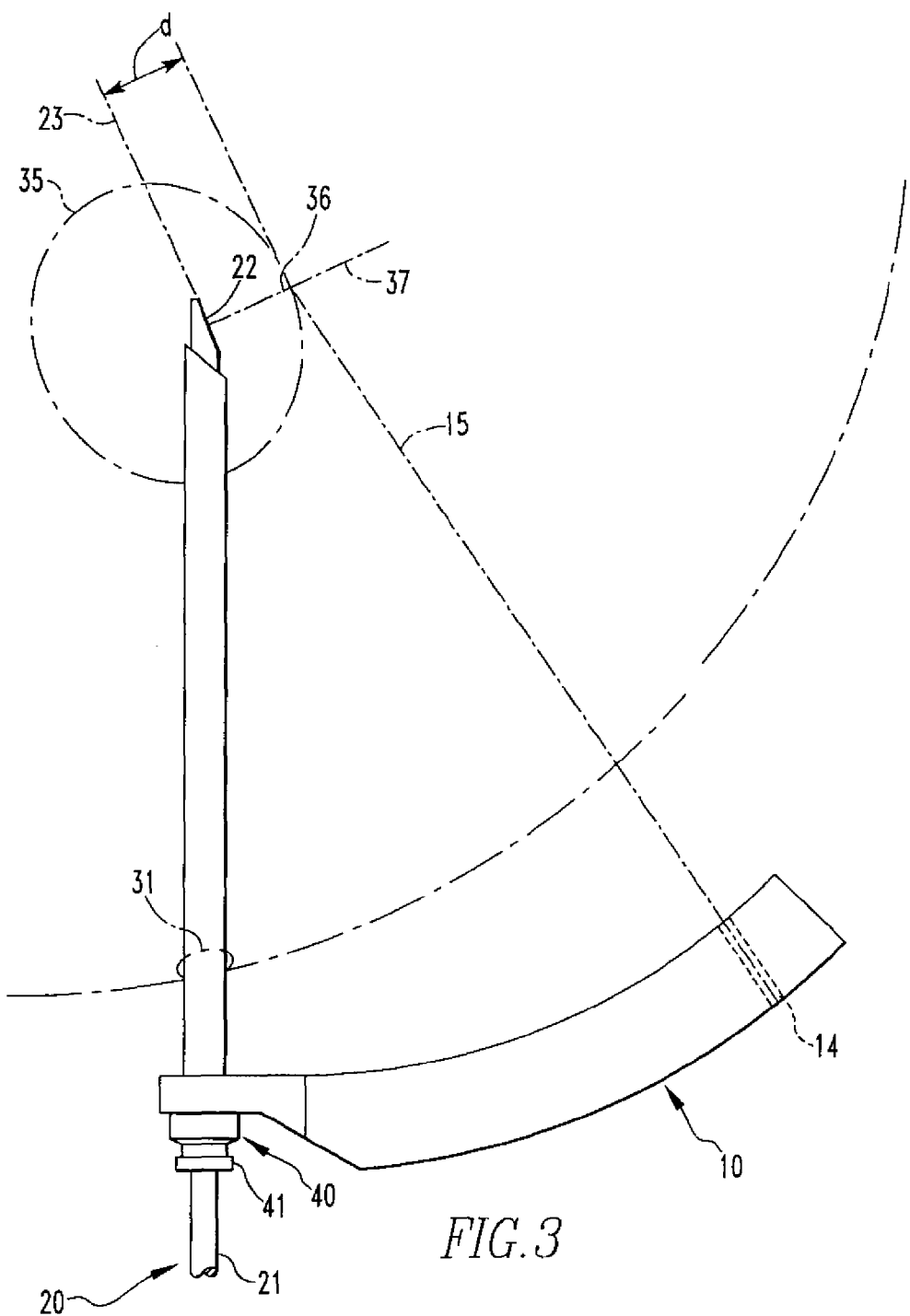

FIG. 3 is similar to FIG. 2 in that a longitudinal axis 15 of the through hole 14 intersects with an area 36 that is offset a distance d from the endoscope 20 or in a direction of view 37 of the endoscope 20. However, rather than using the pointed tip 43 of the cannula 40 to identify this area 36, the average distance d between the endoscope 20 and the point of intersection with area 36 is determined and an offset, equal to that average distance d, is built into the guide 10 so that a longitudinal axis 15 of the through hole 14 intersects with this area 36. For example, during hip arthroscopy, a surgeon may want to introduce a needle into the hip capsule 35, but the hip anatomy may prevent the second end 22 of the endoscope 20 from being brought up against the inner surface 36 of the hip capsule. Since the endoscope 20 may be a distance from the capsule inner surface 36, an error where the needle penetrates the capsule would result. To overcome this problem, the pointed tip 43 or the built-in offset d, as described above, could be used. For the purposes of this disclosure, the distance d is about 1 cm. However, the distance d will vary based on the location of the endoscope 20 relative to area 36.

Figure 4:
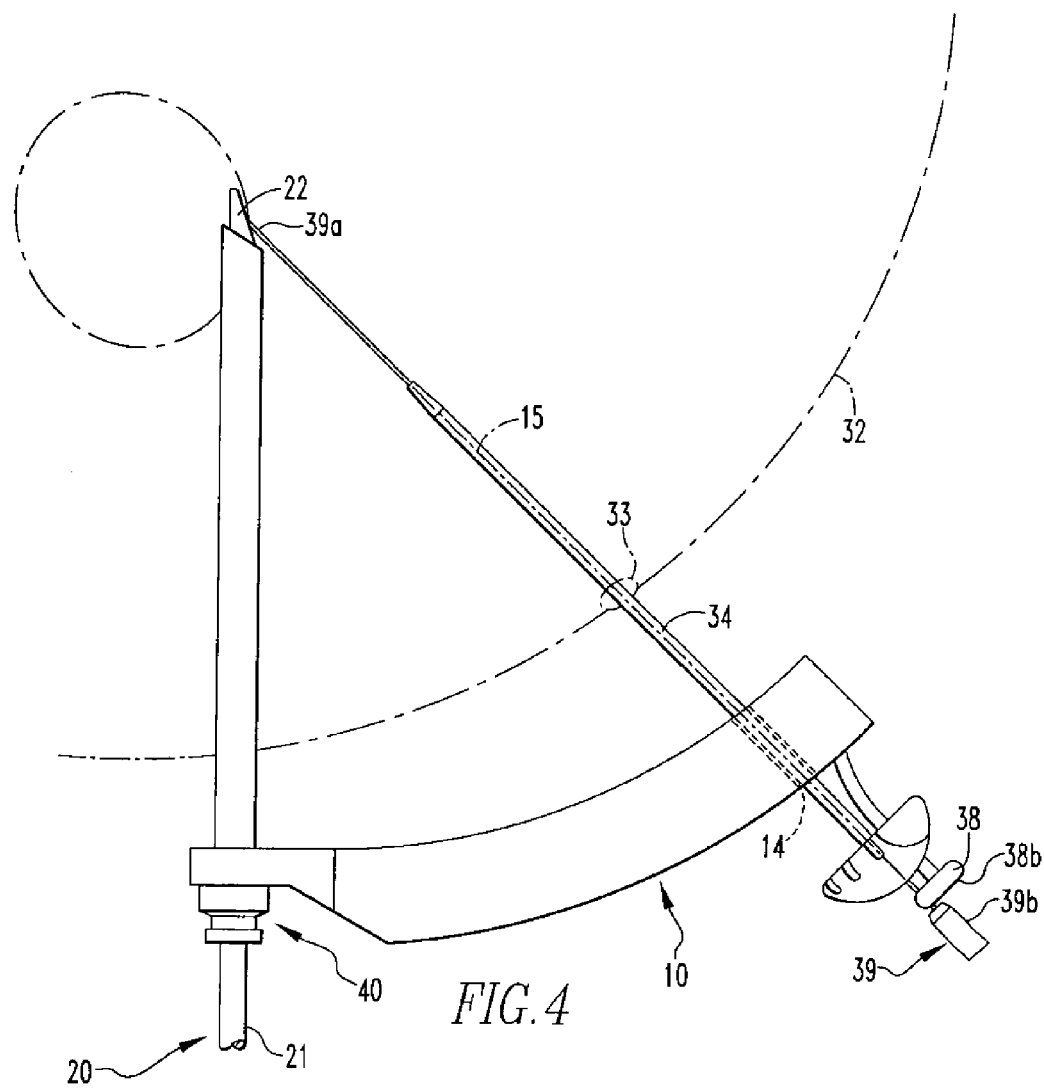

FIG. 4 shows the second cannula 34 disposed within the through hole 14 and second portal 33. The cannula 34 includes a depth stop 38 that substantially reduces the possibility of a first end 39a of a needle 39 or other surgical instrument, disposed within the cannula 34, from advancing past the second end 22 of the endoscope 20 by having a second end 39b of the needle 39 abut a second end 38b of the depth stop 38. The depth stop 38 may be part of the second cannula 34 or separate from the second cannula 34. This allows the second cannula 34 to be positioned to any depth within the through hole 14, yet still have a fixed depth stop relative to the guide 10.

Figure 5:
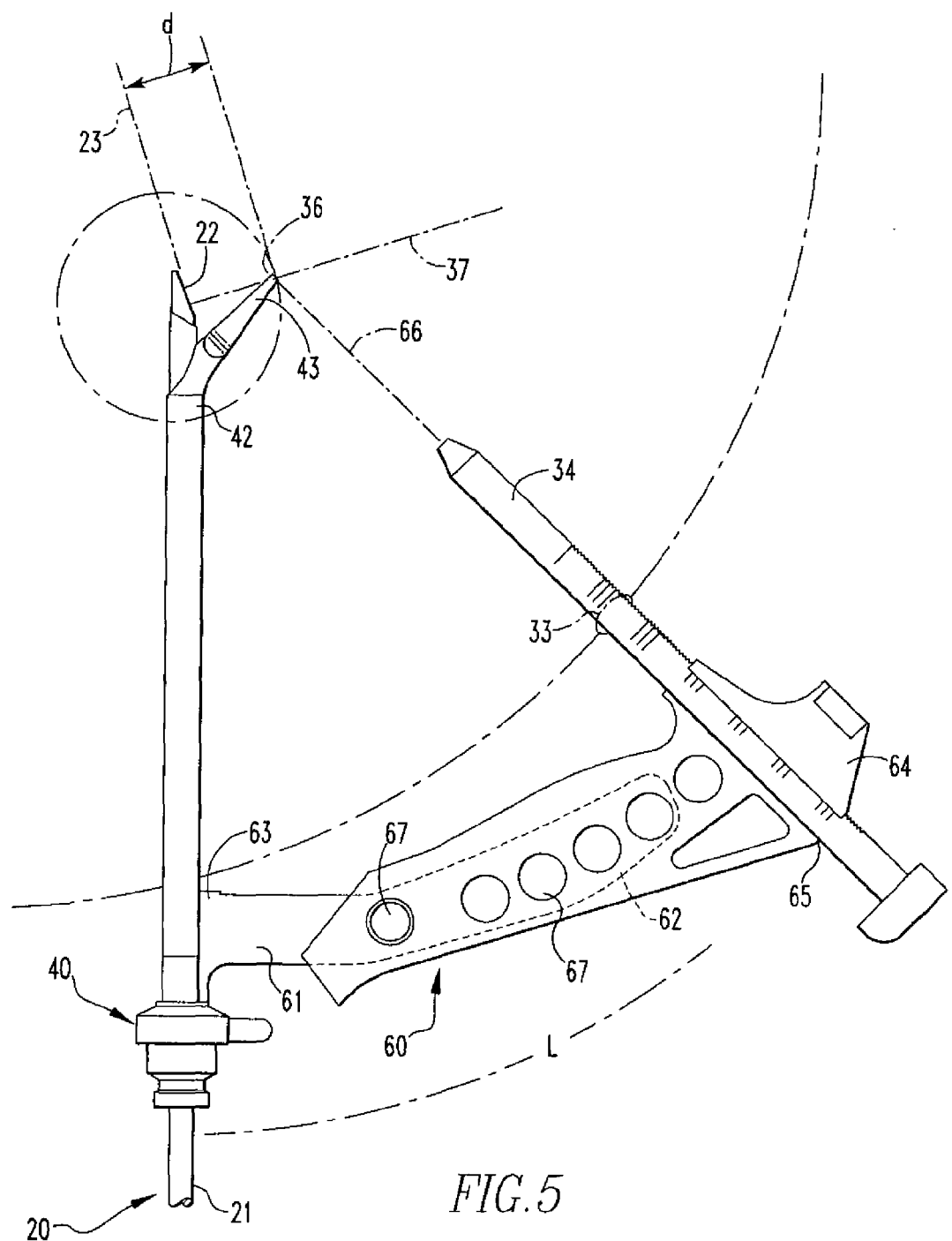
FIG. 5 shows a front view of a second guide assembly of the present disclosure.

FIG. 5 shows a guide 60 that includes a body 61 having a first end 62, a second end 63, and an arc along a length L of the body 61. The guide 60 also includes a joint 64 configured for sliding along the length L of the body 61. The joint 64 includes at least one through hole 65. Similar to the guide 10 disclosed in FIGS. 1-4, guide 60 is also coupled to a first surgical device 20, such as an endoscope. The endoscope 20 may be disposed within a first cannula 40, similar to the first cannula disclosed in FIG. 2 and described above, such that the second end 22 of the endoscope 20 protrudes through a second end 42 of the cannula 40. The cannula 40 has a pointed tip 43 similar to the pointed tip shown in FIG. 2 and described above. A second surgical device 34, similar to the second surgical device shown in FIG. 4, is disposed within the through hole 65. A longitudinal axis 66 of the through hole 65, and therefore of the second surgical device 34, intersects, or is co-radial with, the pointed tip 43. However, the longitudinal axis 66 could be made to intersect, or be co-radial with, the second end 22 of the endoscope 20 or with an area 36 that is offset a distance d from the endoscope 20, as shown in FIGS. 1 and 3.

The joint 64 may be slid along the length L of the body 61 to decide where to place the second portal 33 so that damage to internal structures can be minimized. Since the longitudinal axis 66 of the through hole 65 and the second surgical device 34 is co-radial with the pointed tip 43, a needle or other surgical instrument disposed within the second surgical device 34, will intersect the pointed tip 43, regardless of where the second portal 33 is placed. The joint 64 and the body 61 may include openings 67 to make the guide 60 lightweight and ensure that the joint 64 and body 61 cool quickly after autoclaving.

Figure 6:
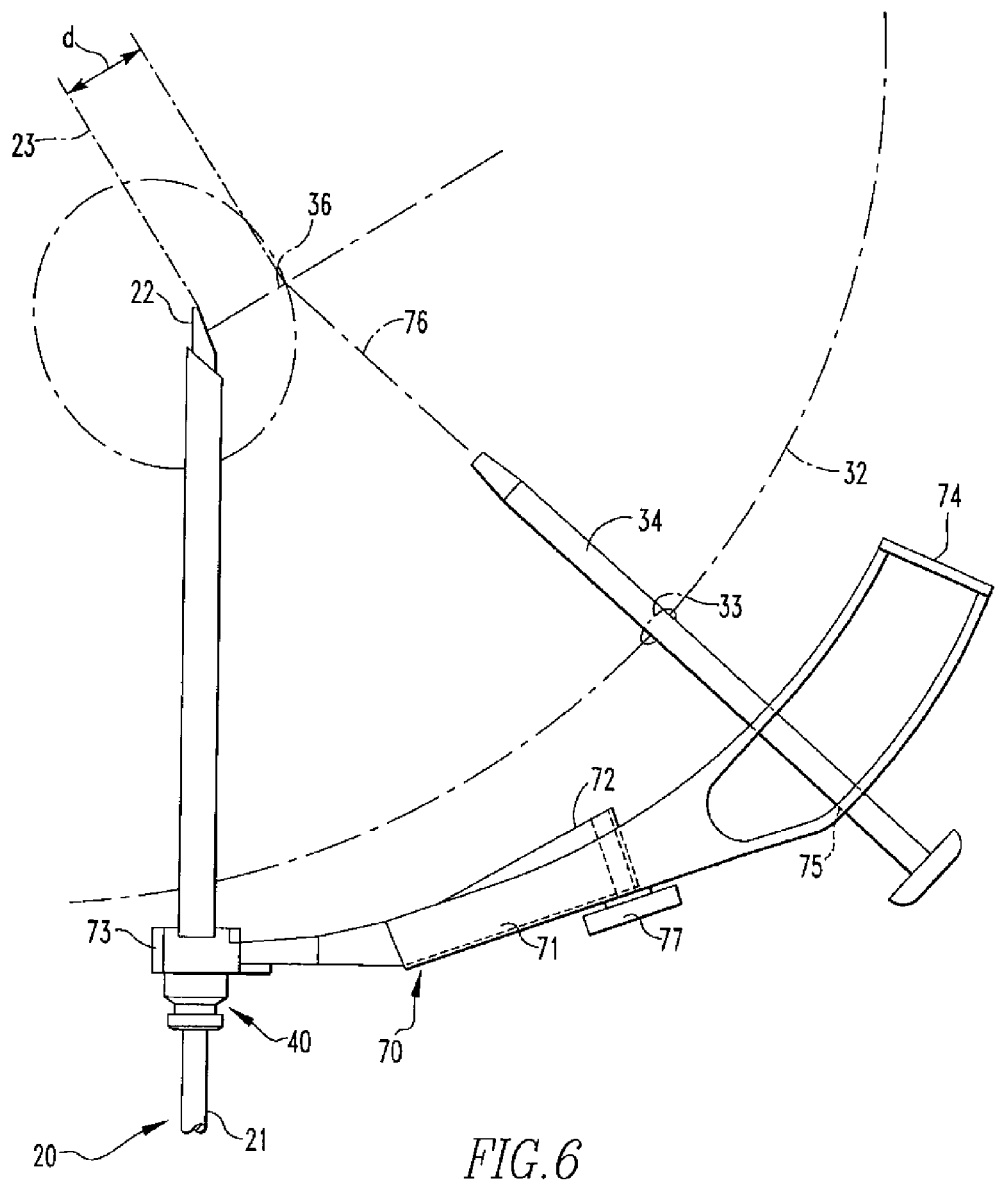
FIG. 6 shows a front view of a third guide assembly of the present disclosure.

Similar to the guide 60 shown in FIG. 5, FIG. 6 shows a guide 70 that includes a body 71 having a first end 72, and a second end 73. The guide 70 also includes a joint 74 configured for sliding along the body 71. The joint 74 includes at least one through hole 75. Similar to the guide 10 disclosed in FIGS. 1-4, guide 70 is also coupled to a first surgical device 20, such as an endoscope, via a cannula 40. A second surgical device 34, similar to the second surgical device shown in FIG. 4, is disposed within the through hole 75. A longitudinal axis 76 of the through hole 75, and therefore of the second surgical device 34, intersects, or is co-radial with, an area 36 that is offset a distance d from the endoscope 20. However, the longitudinal axis 76 could be made to intersect, or be co-radial with, a pointed tip 43 of the cannula 40 or the second end 22 of the endoscope 20, as shown in FIGS. 2, 5, 1 and 4.

As also shown in FIG. 5 and described above, the joint 74 may be slid along the body 71 to vary the distance d based upon the distance between the second end 22 of the endoscope 20 and the capsule inner surface 36. Since the second surgical device 34 is co-radial with the area 36, a needle or other surgical instrument disposed within the second surgical device 34, will intersect the area 36, regardless of where the second portal 33 is placed. The guide 70 also includes a mechanism 77, such as a locking nut, for engaging the joint 74 and holding it in a position along the body 71. Once the surgeon has determined the position of the second portal 33, the locking nut 77 will be tightened to engage the joint 74 and hold it in a position along the body 71. The second surgical device 34 will then be inserted into the through hole 75 and through the patient's body 32 to make the second portal 33.

Figure 7:
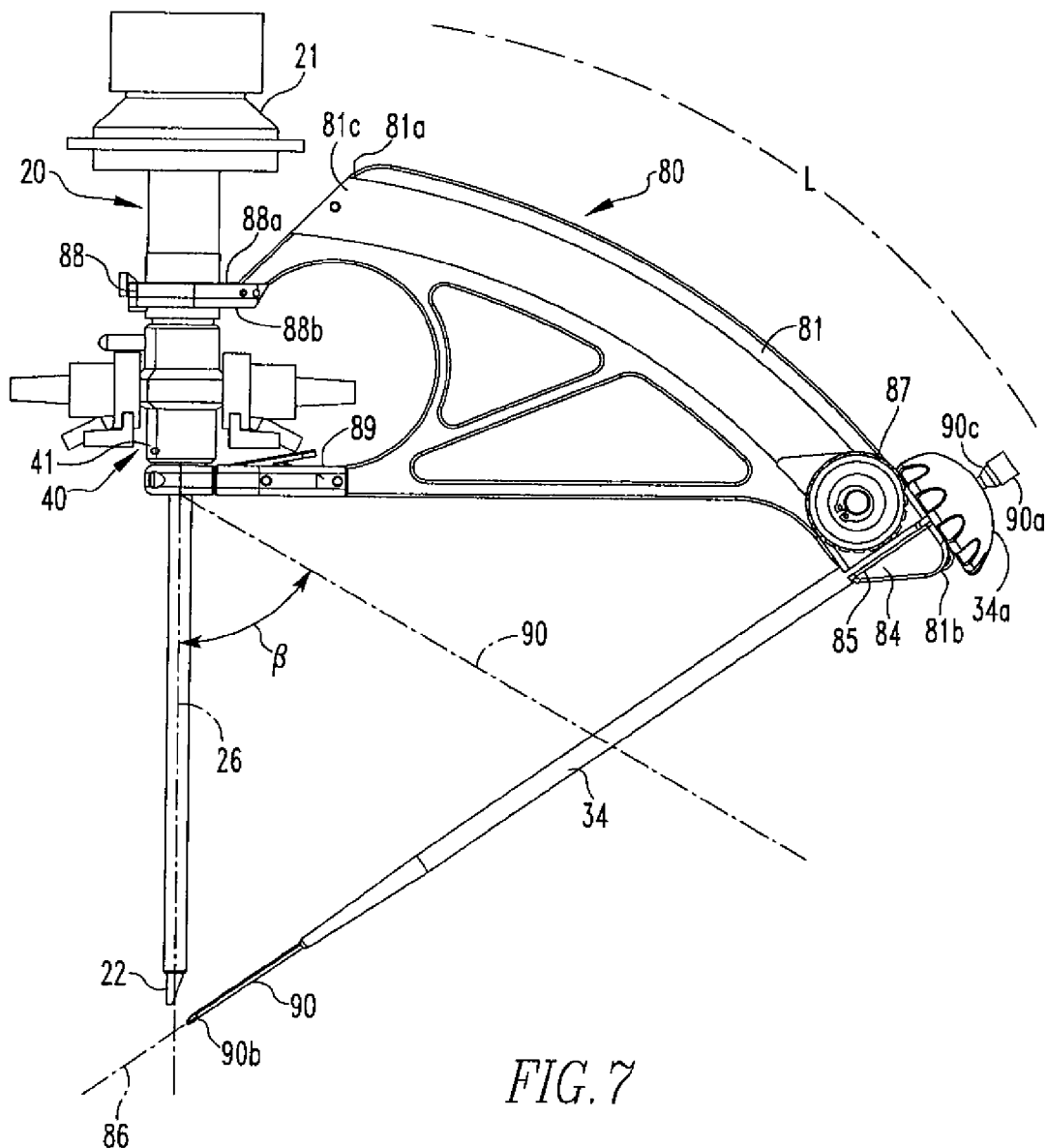
FIG. 7 shows a front view of a fourth guide assembly of the present disclosure.

Similar to the guides 60,70 shown in FIGS. 5 and 6, the guide 80 shown in FIG. 7 includes a body 81 having a first end 81a, a second end 81b, and an arc along a length L of the body 81. The guide 80 also includes a joint 84 configured for sliding along a length L of the body 81. The joint 84 includes at least one through hole 85. Similar to the guide 10,60,70 disclosed in FIGS. 1-6, guide 80 is also coupled to a first surgical device 20, such as an endoscope via the first end 21 of the endoscope 20 and the first end 41 of the cannula 40. A second surgical device 34, similar to the second surgical device shown in FIGS. 4-6, is disposed within the through hole 85. A longitudinal axis 86 of the through hole 85, and therefore of the second surgical device 34, intersects, or is co-radial with, the second end 22 of the endoscope 20. However, the longitudinal axis 86 could be made to intersect, or be co-radial with, a pointed tip 43 of the cannula 40 or an area 36 that is offset a distance d from the endoscope 20, as shown in FIGS. 4, 5, and 3.

As also shown in FIG. 7 and described above, the joint 84 may be slid along the length L of the body 81 to decide where to place a second portal so that damage to internal structures can be minimized. Since the second surgical device 34 is co-radial with the second end 22 of the endoscope 20, a needle 90 or other surgical instrument disposed within the second surgical device 34, will intersect the second end 22, regardless of where the second portal is placed. The body 80 includes a slot 81c that runs the entire length L of the body 80 and that houses the joint 84. In addition, similar to the guide 70 of FIG. 6, the guide 80 includes a mechanism 87, such as a locking nut, for engaging the joint 84 and holding it in a position along the body 81. During surgery, use of the locking nut 87 in creating a second portal occurs in the same manner as described above. After the second surgical device 34, or second cannula, has been inserted into the patient's body, the needle 90, or other instrument, may be inserted through the cannula 34 for use in performing a surgical procedure. The needle 90 which intersects, or is co-radial with, the second end 22 of the endoscope 20, may include a depth stop 90c, at a first end 90a of the needle 90, that abuts a first end 34a of the cannula 34 to substantially reduce the possibility of the second end 90b of the needle 90 from advancing past the second end 22 of the endoscope 20.

Figure 8:
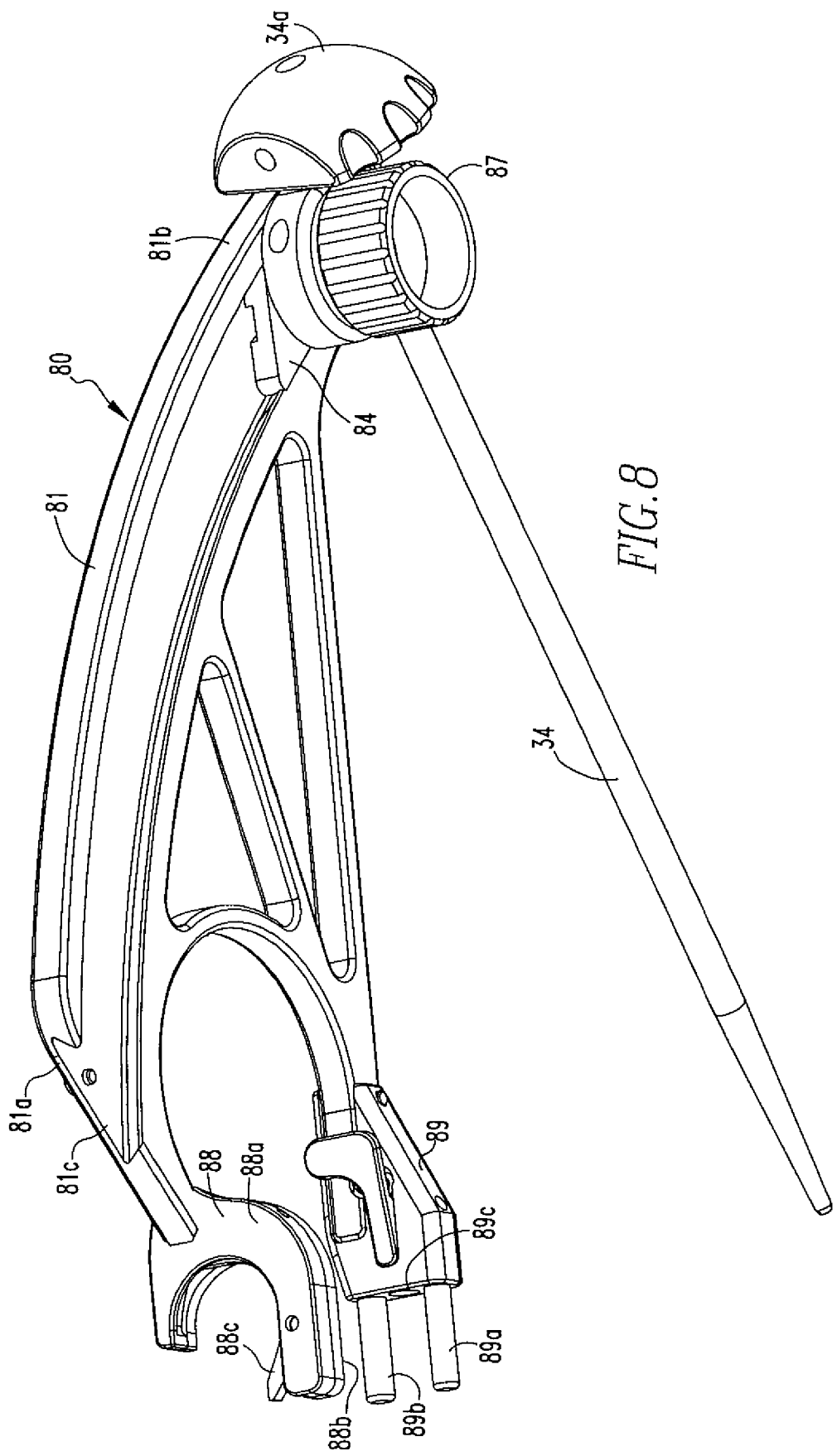
FIG. 8 shows an isometric view of the fourth guide assembly of the present disclosure.
Figure 9B:
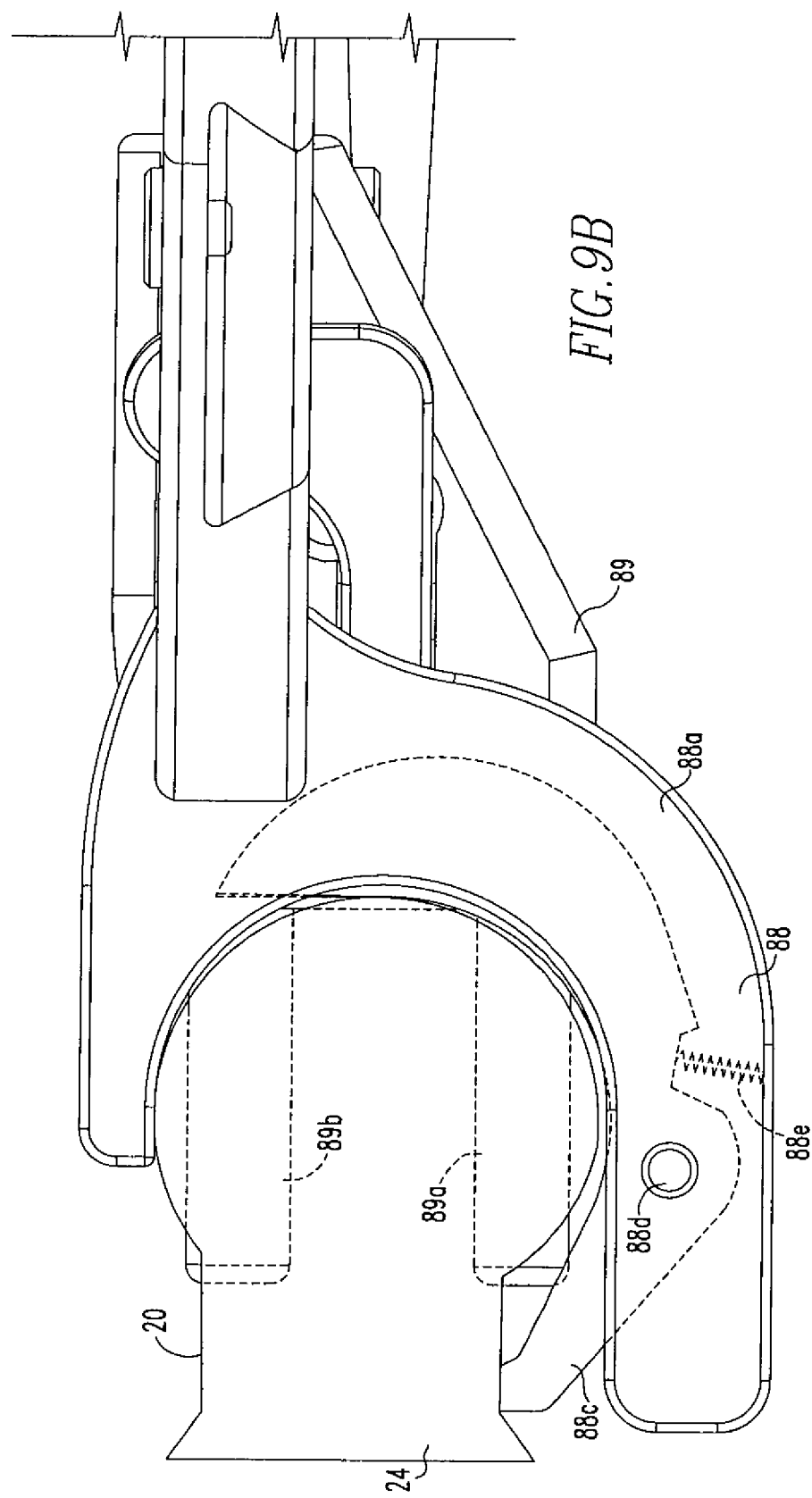
FIG. 9B shows a top view of the lever arm, of the fourth guide assembly, in a second position.

As shown in FIGS. 7 and 8, the guide 80 includes a first attachment portion 88 and a second attachment portion 89, both of which are configured for coupling the body 81 to the first surgical device 20 via the first surgical device 20 and the cannula 40. The first attachment portion 88, which includes an anti-rotation lock, is located at the first end 81a of the body 81 and extends substantially perpendicular to the axis 26 of the endoscope 20. As shown in FIGS. 9A and 9B, the anti-rotation lock 88 includes a lever arm 88c located between a top surface 88a and bottom surface 88b of the anti-rotation lock 88. The lever arm 88c is coupled to the surfaces 88a,b via a pivot pin or screw 88d and a spring 88e. When the endoscope 20 is not coupled to the anti-rotation lock 88, the lever arm 88c is in a first position, as shown in FIG. 9A, such that the spring 88e is in a relaxed state. However, when the endoscope 20 is coupled to the anti-rotation lock 88, the lever arm 88c is in a second position, as shown in FIG. 9B, such that the lever arm 88c is pushed against the light post 24 of the endoscope 20, and substantially reduces the possibility of rotation of the light post 24 in a direction that would uncouple the cannula 40 from the endoscope 20.

Figure 10:
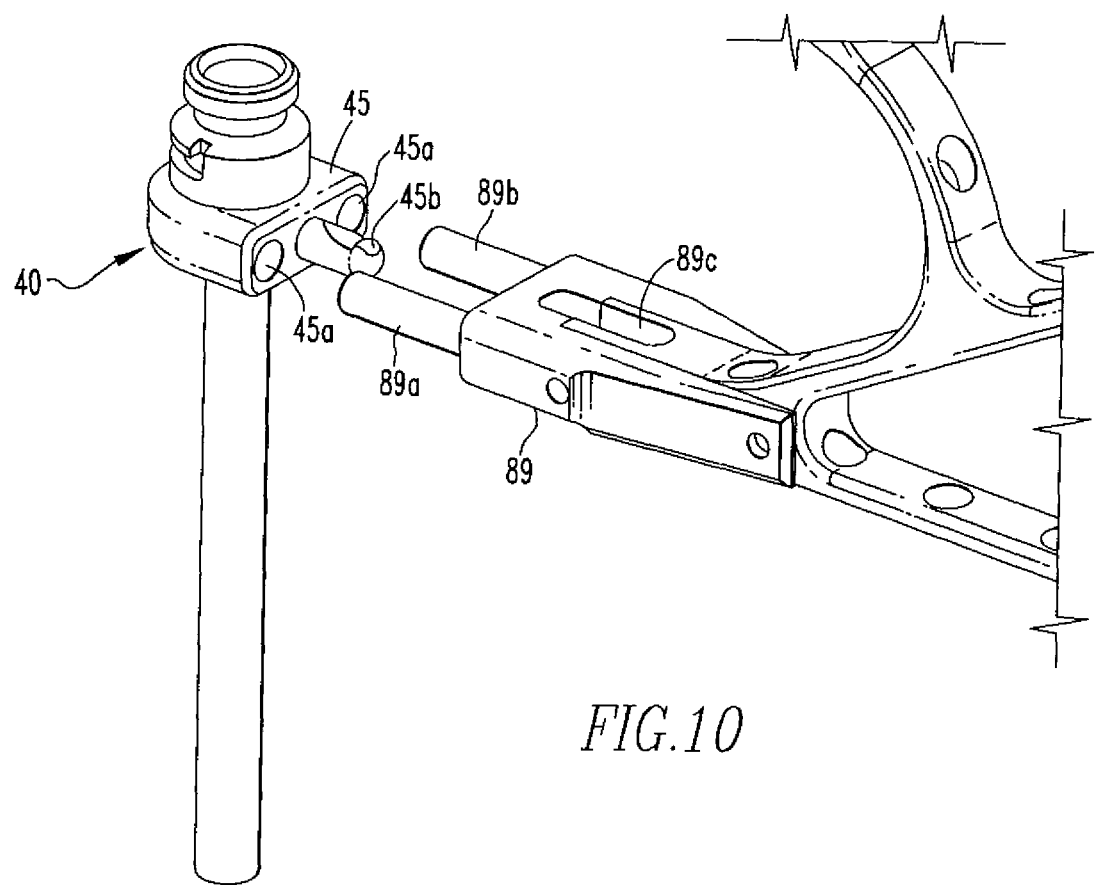
FIG. 10 shows a perspective view of the second attachment portion of the fourth guide assembly.

As shown in FIGS. 7 and 8, the second attachment portion 89 is located near the second end 81b of the body 81 and extends substantially perpendicular to the longitudinal axis 26 of the endoscope 20. The portion 89 includes two prongs 89a,b, both of which extend longitudinally from the portion 89, and an opening 89c, located between the prongs 89a,b that extends longitudinally into the portion 89. As shown in FIG. 10, the cannula 40 includes a coupling portion 45 configured for coupling of the second attachment portion 89 to the cannula 40. The coupling portion 45 includes two holes 45a and a projection 45b that extends longitudinally from the coupling portion 45. The second attachment portion 89 is coupled to the coupling portion 45 such that the prongs 89a,b are disposed within the holes 45a and the projection 45b is disposed within the opening 89c.

As shown in FIG. 7, the second end 81b of the body 81 does not extend beyond a plane 90, located between the second attachment portion 89 and a longitudinal axis 26 of the first surgical device 20, and that forms an angle β, about 60°, with the longitudinal axis 26.

Figure 11A:
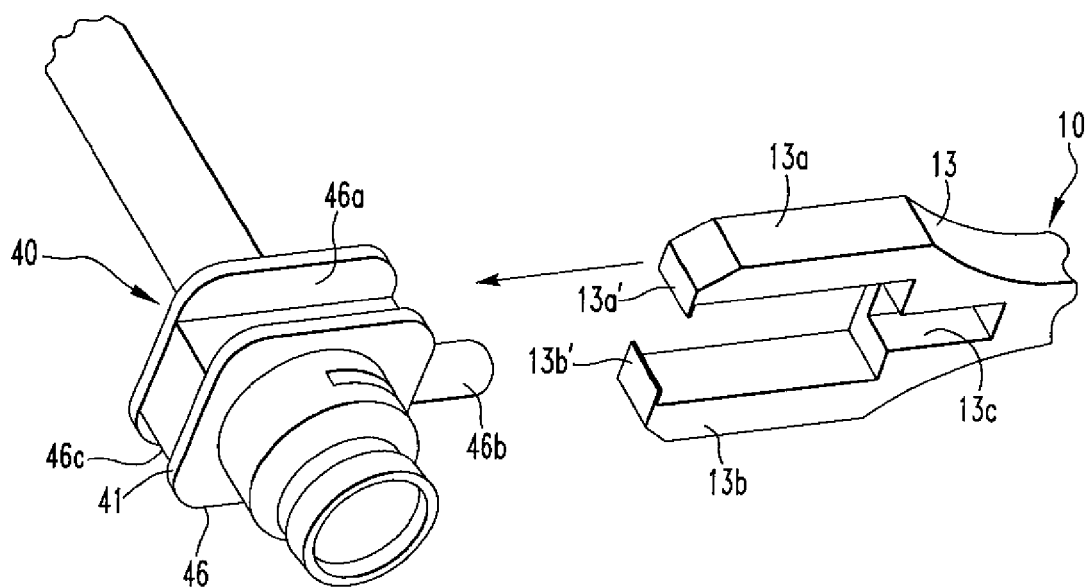
FIGS. 11A-11D show perspective views of methods for attaching the guides of the present disclosure to an endoscope cannula.
Figure 11B:
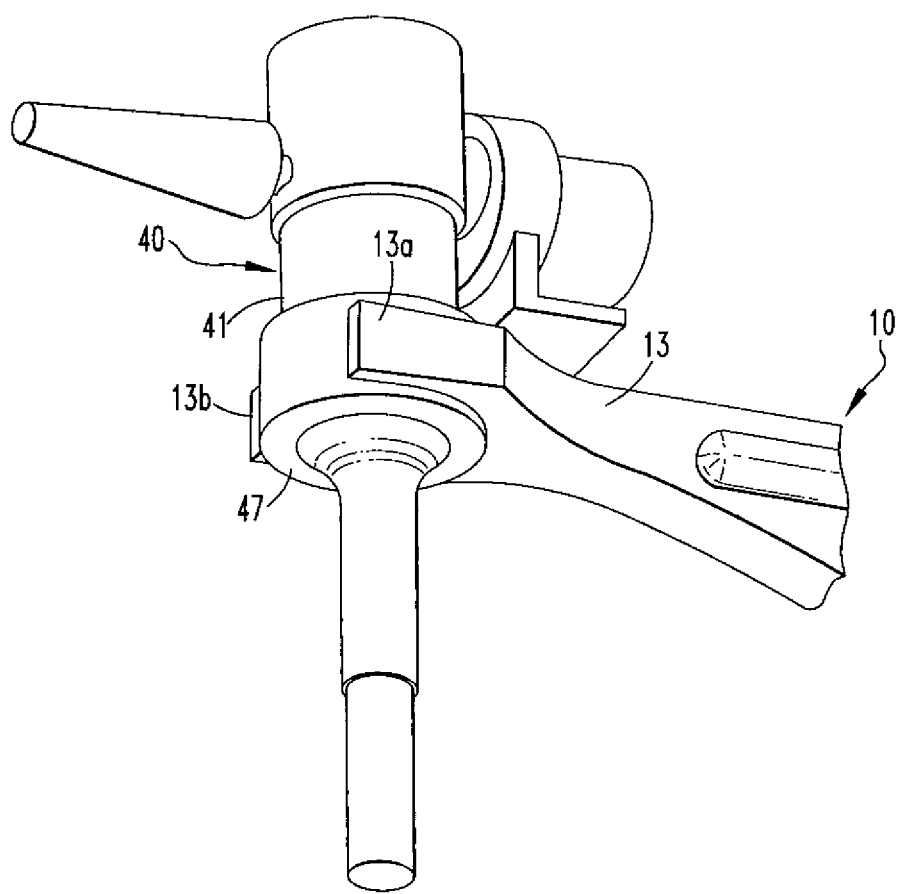
Figure 11C:
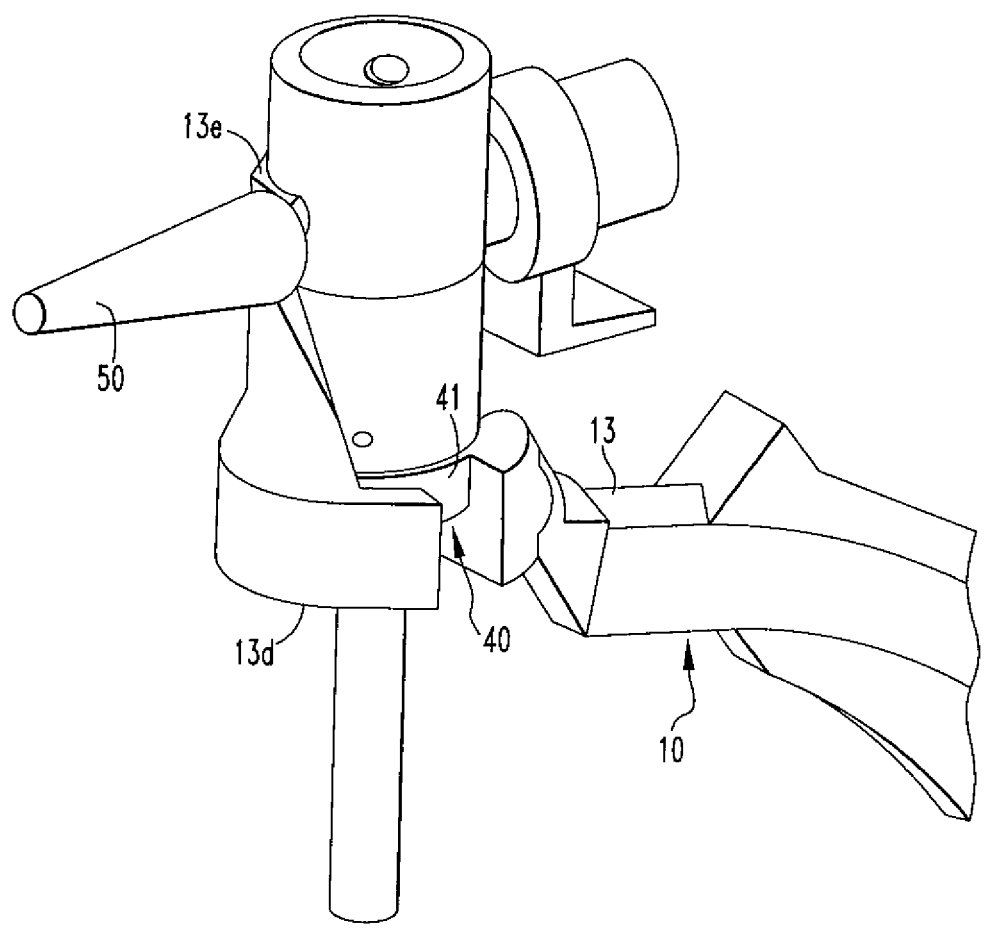

FIGS. 11A-11D show methods for coupling the second end 13 of the guide 10 to the first end 41 of the cannula 40. As shown in FIG. 11A, the second end 13 includes a first arm 13a, a second arm 13b, and a slot 13c located between the first and second arms 13a,b. The first end 41 of the cannula 40 includes a coupling portion 46, similar to the coupling portion 45 shown in FIG. 10 albeit with channels 46a instead of holes 45a. The second end 13 of the guide 10 is coupled to the first end 41 of the cannula 40 such that the first and second arms 13a,b are housed within the channels 46a and the projection 46b is housed within the slot 13c. Both arms 13a,b include an edge 13a', 13b', wherein each edge 13a', 13b' is configured for attaching to the backside 46c of the coupling portion 46 when the guide 10 is coupled to the coupling portion 46, therefore creating a snap-fit connection between the arms 13a,b and the coupling portion 46.

As shown in 11B, the second end 13 of the guide 10 includes a first arm 13a and a second arm 13b. The first end 41 of the cannula 40 includes an adaptor 47 that has been slid over the cannula 40. The first and second arms 13a,b of the guide 10 are coupled to the adaptor 47 such that an interference fit, or a clip-on connection, is created between the arms 13a,b and the adaptor 47.

Figure 11D:
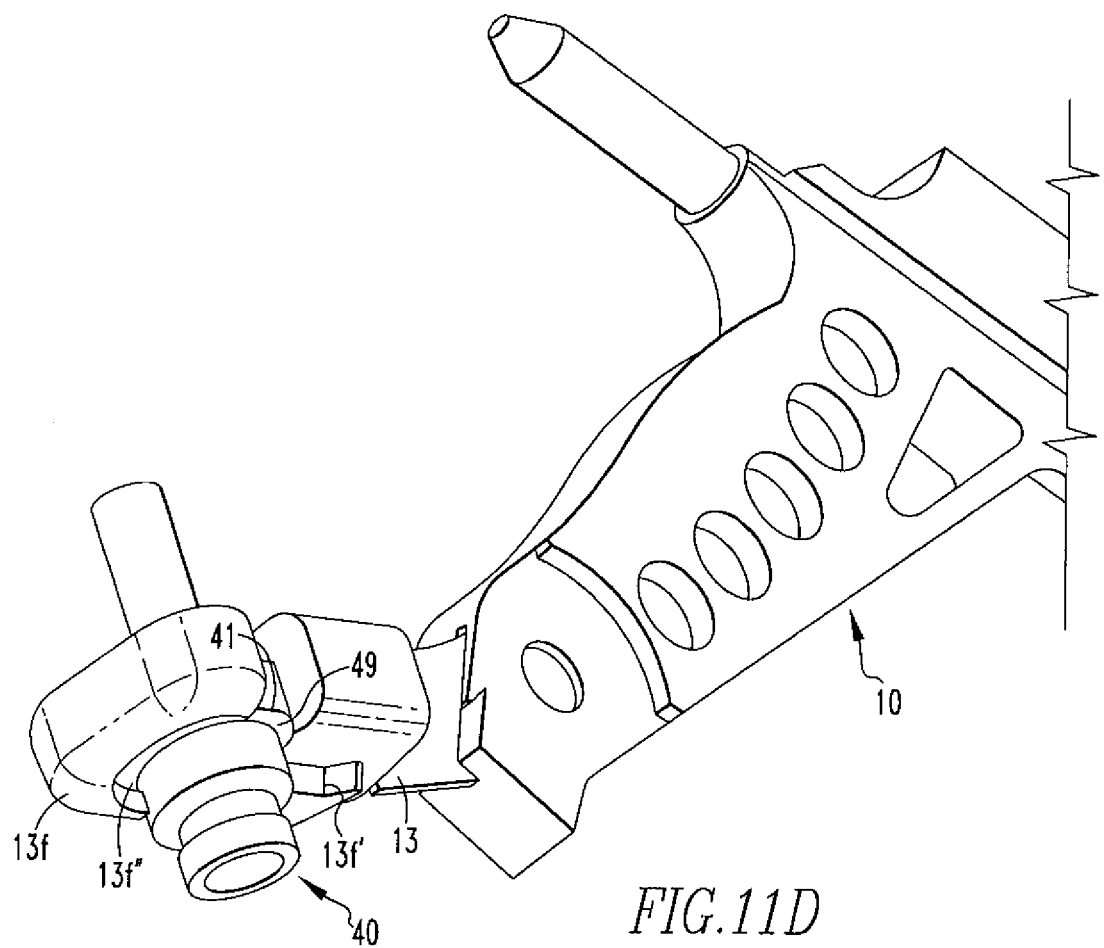

As shown in 11C, the second end 13 of the guide 10 includes a base portion 13d that partially surrounds the first end 41 of the cannula 40 and includes a hook 13e that is placed on the irrigation extender 50, which is coupled to the cannula 40. Shown in FIG. 11D is a guide 10 that includes a second end 13 having an arm 13f including an opening 13f'' and a slot 13f' formed in the arm 13f. The first end 41 of the cannula 40 includes a coupling portion 49, similar to the coupling portions 45, 46 shown in FIGS. 10 and 11A, albeit without holes or channels. The second end 13 of the guide 10 is coupled to the first end 41 of the cannula 40 such that the first end 41 of the cannula 40 is disposed within the opening 13f'' and the projection (not shown) is housed within the slot 13f. The guide 10 may be placed onto the first end 41 by placing the opening 13f'' over the first end 41 and sliding the arm 13f around the coupling portion 49, so as to create a snap-fit connection between the arm 13f and the first end 41. Other methods of coupling the guide to the cannula may also be used.

Figure 12:
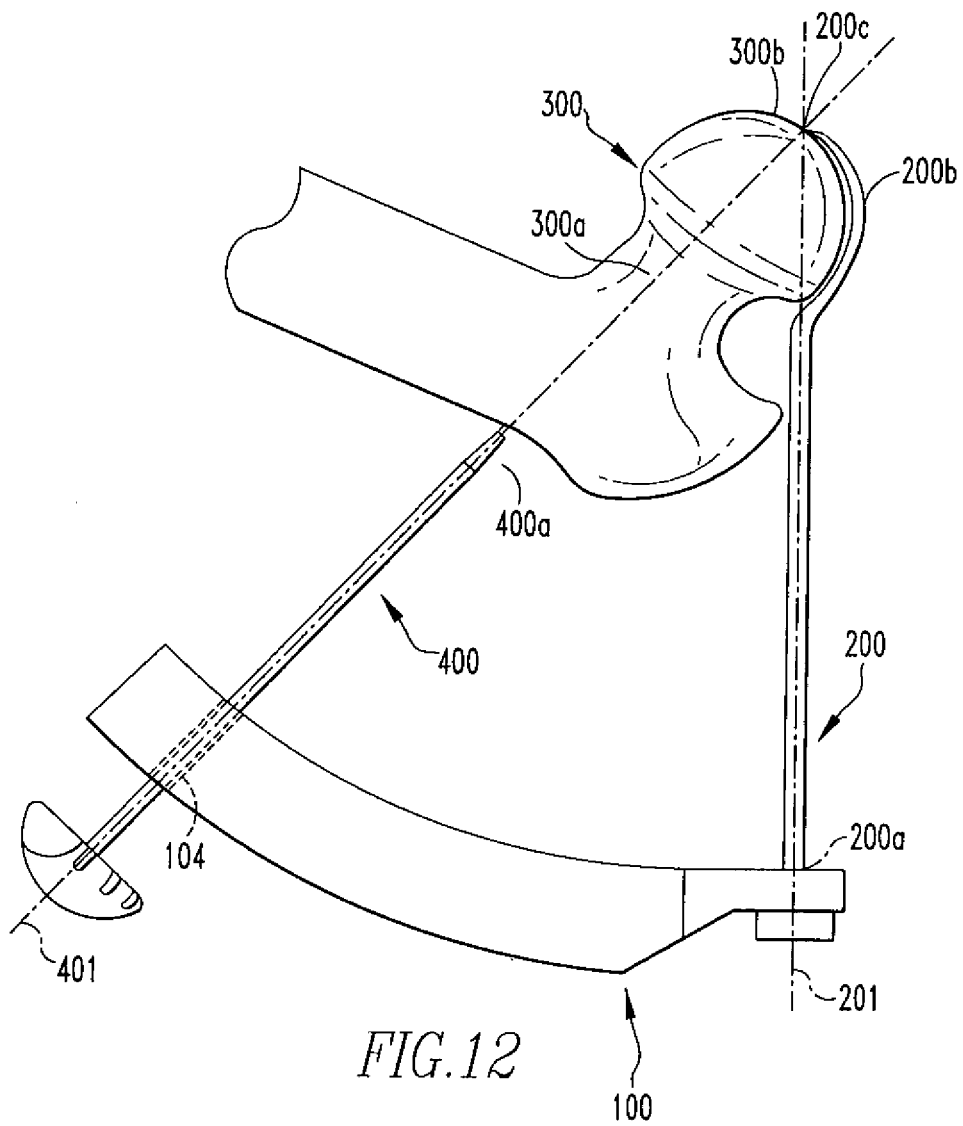
FIG. 12 shows a front view of the first guide of the present disclosure coupled to an aimer arm.

As shown in FIG. 12, a guide 100, similar to the guide 10 in FIGS. 1-4, is coupled to a first surgical device 200, such as an aimer arm, that includes a distal end 200b in the shape of a hook. The distal end 200b of the aimer arm 200 is positioned in the posterior region 300b of the hip joint 300. A second surgical device 400, such as a cannula, is disposed within the through hole 104 of the guide 100. A longitudinal axis 401 of the cannula 400 is co-radial with the tip 200c on the distal end 200b of the aimer arm 200. This co-radial relationship allows access to the posterior region 300b of the hip joint 300, via the femoral neck 300a, by a surgical tool, such as a drill (not shown), disposed within the cannula 400. The aimer arm 200 may be introduced into the body 32 in the same manner as the endoscope 20 is introduced, as described above, or another manner known to one of ordinary skill in the art. Likewise, the guide 100 may be coupled to the aimer arm 200 in the same manner as guide 80 is coupled to the cannula 40 in FIG. 7, in the same manner as guide 10 is coupled to the cannula 40 in FIGS. 11A-11D, or another manner known to one of ordinary skill in the art. The aimer arm 200 may rotate around a longitudinal axis 201 of the aimer arm 200 via a rotational coupling (not shown) located at the proximal end 200a of the aimer arm 200.

For the purposes of this disclosure, a manual or automatic milling machine is used to create the through holes of the guides described above. Other apparatuses and methods of creating the through holes may also be used. The guides are manufactured from a metal material, such as stainless steel or titanium, but may be manufactured from another material known to one of ordinary skill in the art. In addition, the first and second cannulas and the aimer arm described above are manufactured from a biocompatible metal material, such as stainless steel, but may be manufactured from another biocompatible material known to one of ordinary skill in the art. Furthermore, for the purposes of this disclosure, the guides include a body having an arc along the length of the body, but an arc is not necessary and the body may be straight or incorporate any other shapes known to one of ordinary skill in the art. Although the present disclosure relates to the use of the above described guides for the placement of portals during hip arthroscopy, the basic principles and methods may also be applied to other joint areas of the body.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A guide assembly comprising:
   a guide including a body and a joint including at least one through hole, the joint configured for sliding along the length of the body; and
   a first surgical device, defining a longitudinal axis,
   wherein the guide is directly attached to the first surgical device at a first attachment portion and directly attached at a second attachment portion to a first cannula housing the first surgical device, and
   wherein a longitudinal axis of the through hole is co-radial with an end of the first surgical device, the through hole being configured to receive a second surgical device for simultaneous use with the first surgical device;
   wherein the longitudinal axes define a plane and the longitudinal axes remain substantially in the plane throughout a range of motion of the joint along the length of the body; and
   wherein the first attachment portion includes a lever arm configured to contact a surface of the first surgical device that is perpendicular to the longitudinal axis of the first surgical device to attach the first surgical device to the first attachment portion.

2. The guide assembly of claim 1 further for locking the joint in a position along the body.

3. The guide assembly of claim 1 further comprising a second surgical device disposed within the through hole, the second surgical device including a longitudinal axis that is co-radial with the end of the first surgical device.

4. The guide assembly of claim 1 wherein an end of the first surgical device protrudes through an end of the first cannula.

5. The guide assembly of claim 1 wherein the longitudinal axis of the through hole is co-radial with a point that is offset a distance from the end of the first surgical device.

6. The guide assembly of claim 5 wherein the first surgical device includes an endoscope, the point offset a distance in a direction of view of the endoscope.

7. The guide assembly of claim 3 wherein the second surgical device includes a second cannula.

8. The guide assembly of claim 7 wherein the second cannula includes a needle, the needle having a first end and a second end and being slidably disposed within the second cannula.

9. The guide assembly of claim 8 wherein the second end intersects with the end of the first surgical device.

10. The guide assembly of claim 8 wherein the first end includes a depth stop.

11. The guide assembly of claim 1 wherein first attachment portion is located at a first end of the body and a second attachment portion is located near a second end of the body.

12. The guide assembly of claim 11 wherein the second end of the body does not extend beyond a plane located between the second attachment portion and a longitudinal axis of the first surgical device.

13. The guide assembly of claim 12 wherein an angle exists between the longitudinal axis of the first surgical device and the plane.

14. The guide assembly of claim 1 wherein the lever arm is movable between a first position and a second position with respect to the first attachment portion.

15. The guide assembly of claim 14 wherein the first surgical device is attached to the first attachment portion when the lever arm is in a second position.

16. The guide assembly of claim 1 wherein an end of the first cannula includes a pointed tip, the pointed tip offset a distance from an end of the first surgical device.

17. The guide assembly of claim 16 wherein the first surgical device includes an endoscope, the pointed tip offset a distance in a direction of view from the endoscope.

18. The guide assembly of claim 10 wherein the second end of the needle does not advance past the end of the first surgical device.

19. The guide assembly of claim 1 wherein the first attachment portion is forked about an axis perpendicular to the longitudinal axis defined by the first surgical device, the first attachment portion comprising:
   a first tine and a second tine shorter in length than the first tine, the first tine including a pivot about which the lever arm pivots to couple the first surgical device to the first attachment portion; and
   an arcuate portion extending between opposing faces of the first and second tines.

20. The guide assembly of claim 1 wherein the first attachment portion is perpendicular to the longitudinal axis defined by the first surgical device;
   wherein the first attachment portion includes a first surface and a second surface; and
   wherein the lever arm is coupled to the first and second surfaces by a pivot pin and a spring.

21. The guide assembly of claim 1 wherein the first attachment portion is perpendicular to the longitudinal axis defined by the first surgical device;
   wherein the first attachment portion includes a first surface and a second surface; and
   wherein the lever arm is coupled to the first and second surfaces by a screw and a spring.

22. The guide assembly of claim 1 wherein the first surgical device is an endoscope with a light post; and
wherein the lever arm includes a flat portion configured to contact the light post and a arcuate portion configured to contact the endoscope.

23. The guide assembly of claim 1 wherein the second attachment portion is perpendicular to the longitudinal axis defined by the first surgical device.

24. The guide assembly of claim 1 wherein the second attachment portion includes two prongs extending longitudinally, the two prongs configured to be disposed within two corresponding holes in the first cannula housing the first surgical device; and
an opening located between the two prongs, the opening extending longitudinally into the second attachment portion and configured to receive a corresponding projection of the first cannula housing the first surgical device.

25. The guide assembly of claim 1 wherein the second attachment portion includes two arms extending longitudinally, the arms prongs configured to be housed within two corresponding channels in the first cannula housing the first surgical device; and
an slot located between the two arms, the slot extending longitudinally into the second attachment portion and configured to receive a corresponding projection of the first cannula housing the first surgical device.

26. The guide assembly of claim 1 wherein the guide includes an edge extending between the first and second attachment portions, the edge forming a concavity that provides clearance for irrigation extenders coupled to the first cannula housing the first surgical device.

27. A guide assembly comprising:
a guide including a body and a joint including at least one through hole, the joint configured for sliding along the length of the body; and
a first surgical device, defining a longitudinal axis,
wherein the guide is directly attached to the first surgical device at an attachment portion, and
wherein a longitudinal axis of the through hole is co-radial with an end of the first surgical device, the through hole being configured to receive a second surgical device for simultaneous use with the first surgical device, and
wherein the longitudinal axes define a plane and the longitudinal axes remain substantially in the plane throughout a range of motion of the joint along the length of the body; and
wherein the attachment portion includes a lever arm configured to contact a surface of the first surgical device that is perpendicular to the longitudinal axis of the first surgical device to attach the first surgical device to the attachment portion.

28. The guide assembly of claim 27 wherein the guide is further directly attached at a second attachment portion to a first cannula housing the first surgical device.

29. A guide comprising:
an arcuate body having a first end, a second end, and a longitudinal axis extending between the first and second ends;
a first attachment portion located at the first end of the body and extending longitudinally, the first attachment portion includes a lever arm configured to contact a surface of a first surgical device that is perpendicular to a longitudinal axis of the first surgical device to attach the first surgical device to the first attachment portion;
a second attachment portion located near the second end of the body and extending longitudinally, the second attachment portion includes two prongs extending longitudinally, the two prongs configured to be disposed within two corresponding holes in a first cannula housing the first surgical device, the second attachment portion further includes an opening located between the two prongs, the opening extending longitudinally into the second attachment portion and configured to receive a corresponding projection of the first cannula;
a joint configured for sliding along a length of the body, the joint including a through hole configured to receive a second cannula.

30. A kit comprising:
the guide of claim 29;
a first cannula attached to the first attachment portion of the guide; and
a second cannula disposed within the through hole of the joint.

* * * * *